US008481227B2

(12) United States Patent
Hamrock et al.

(10) Patent No.: US 8,481,227 B2
(45) Date of Patent: Jul. 9, 2013

(54) PROTON CONDUCTING MATERIALS

(75) Inventors: Steven J. Hamrock, Stillwater, MN (US); Mark S. Schaberg, Lake Elmo, MN (US); Neeraj Sharma, Woodbury, MN (US); John E. Abulu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/529,706

(22) Filed: Jun. 21, 2012

(65) Prior Publication Data

US 2012/0276471 A1 Nov. 1, 2012

Related U.S. Application Data

(62) Division of application No. 13/269,907, filed on Oct. 10, 2011, now Pat. No. 8,227,140, which is a division of application No. 12/429,371, filed on Apr. 24, 2009, now abandoned.

(60) Provisional application No. 61/047,643, filed on Apr. 24, 2008.

(51) Int. Cl.
*H01M 8/10* (2006.01)
*C07F 9/22* (2006.01)
*C07F 9/28* (2006.01)

(52) U.S. Cl.
USPC ............. 429/494; 429/492; 429/493; 521/27; 562/11

(58) Field of Classification Search
USPC .......... 429/479, 491–494; 521/27, 32; 562/11
See application file for complete search history.

(56) References Cited

U.S. PATENT DOCUMENTS

| 5,246,901 | A | | 9/1993 | Sanderson |
|---|---|---|---|---|
| 5,463,005 | A | | 10/1995 | Desmarteau |
| 5,648,434 | A | * | 7/1997 | Szita et al. ................... 525/441 |
| 5,919,583 | A | | 7/1999 | Grot |
| 6,063,522 | A | | 5/2000 | Hamrock |
| 6,090,895 | A | * | 7/2000 | Mao et al. .................. 525/330.9 |
| 6,624,328 | B1 | | 9/2003 | Guerra |
| 6,683,209 | B2 | | 1/2004 | Hamrock |
| 6,727,386 | B2 | | 4/2004 | Hamrock |
| 6,863,838 | B2 | | 3/2005 | Hamrock |
| 7,060,738 | B2 | | 6/2006 | Jing |
| 7,060,756 | B2 | | 6/2006 | Jing |
| 7,074,841 | B2 | | 7/2006 | Yandrasits |
| 7,112,614 | B2 | | 9/2006 | Jing |
| 7,173,067 | B2 | | 2/2007 | Guerra |
| 7,179,847 | B2 | | 2/2007 | Yandrasits |
| 7,259,208 | B2 | | 8/2007 | Guerra |
| 7,265,162 | B2 | | 9/2007 | Yandrasits |
| 7,285,349 | B2 | | 10/2007 | Hamrock |
| 7,285,616 | B2 | | 10/2007 | Yoshimura |
| 7,326,737 | B2 | | 2/2008 | Guerra |
| 7,348,088 | B2 | | 3/2008 | Hamrock |
| 7,411,022 | B2 | | 8/2008 | Guerra |
| 7,435,498 | B2 | | 10/2008 | Yandrasits |
| 7,514,481 | B2 | | 4/2009 | Yandrasits |
| 8,137,828 | B2 | | 3/2012 | Pierpont |
| 8,206,874 | B2 | | 6/2012 | Hamrock |
| 8,227,140 | B2 | | 7/2012 | Hamrock |
| 2002/0187377 | A1 | * | 12/2002 | Shinoda et al. ................ 429/33 |
| 2003/0013817 | A1 | | 1/2003 | Lu |
| 2004/0116742 | A1 | | 6/2004 | Guerra |
| 2004/0122256 | A1 | * | 6/2004 | Ikeda et al. ..................... 562/1 |
| 2006/0166047 | A1 | * | 7/2006 | Yoshimura et al. ............ 429/12 |
| 2006/0182678 | A1 | * | 8/2006 | Shinoda et al. ............... 423/414 |
| 2006/0275636 | A1 | | 12/2006 | Yang |
| 2009/0269644 | A1 | | 10/2009 | Hamrock |

FOREIGN PATENT DOCUMENTS

| WO | WO 99/61141 | 12/1999 |
|---|---|---|
| WO | WO 03/035611 | 5/2003 |
| WO | WO 03/081691 | 10/2003 |
| WO | WO 2004/106349 | 12/2004 |
| WO | WO 2009/132241 | 10/2009 |

OTHER PUBLICATIONS

L.A. Ford, D.D. DesMarteau , D.W. Smith Jr. Perfluorocyclobutyl (PFCB) aromatic polyethers: Synthesis and characterization of new sulfonimide containing monomers and fluoropolymers, J. Fluorine Chem. 2005, 126,653-660.*

Alberti, "Protonic Conductivity of Layered Zirconium Phosphonates Containing—$SO_3H$ Groups. I. Preparation and Characterization of a Mixed Zirconium Phosphonate of Composition $Zr(O_3PR)_{0.73}$ $(O_3PR')_{1.27} \cdot nH_2O$, with R= -$C_6H_4$-$SO_3H$ and R' =-$CH_2$-OH", Solid State Ionics, 1992, vol. 50, Issues 3-4, pp. 315-322.

Alberti, "Protonic Conductivity of Layered Zirconium Phosphonates Containing -$SO_3H$ Groups. III. Preparation and Characterization of γ-zirconium Sulfoaryl Phosphonates", Solid State Ionics, 1996, vol. 84, Issues 1-2, pp. 97-104.

Cowan, "Dodecatungstoaluminic Acid and its Monolacunary and Mixed-Addendum Derivatives", Inorganic Syntheses, 1990, vol. 33, pp. 18-26.

Hansen, "Reactions of 1,2-Benzenedisulfinic Anhydride", The Journal of Organic Chemistry, Sep. 9, 1983, vol. 48, No. 18, pp. 2943-2949.

Hickner, "Alternative Polymer Systems for Proton Exchange Membranes (PEMs)", Chemical Reviews, 2004, vol. 104, No. 10, pp. 4587-4611.

Judeinstein, "Synthesis and Multispectroscopic Characterization of Organically Modified Polyoxometalates", Journal of the Chemical Society, Dalton Transactions, 1991, Issue 8, pp. 1991-1997.

Judeinstein, "Synthesis and Properties of Polyoxometalates Based Inorganic-Organic Polymers", Chem. Mater., Jan. 1992, vol. 4, No. 1, pp. 4-7.

Katsoulis, "A Survey of Applications of Polyoxometalates", Chemical Reviews, 1998, vol. 98, No. 1, pp. 359-387.

(Continued)

*Primary Examiner* — Carlos Barcena
(74) *Attorney, Agent, or Firm* — Gregory D. Allen

(57) ABSTRACT

Materials are provided that may be useful as ionomers or polymer ionomers, including compounds including bis sulfonyl imide groups which may be highly fluorinated and may be polymers.

17 Claims, No Drawings

OTHER PUBLICATIONS

Kim, "Synthesis, Structure, Spectroscopic Properties, and Hydrolytic Chemistry of Organophosphonoyl Polyoxotungstates of Formula $[C_6H_5P(O)]_2X^{n+}W_{11}O_{39}^{(8-n)-}$ ($X^{n+}= P^{5+}$, $Si^{4+}$)", Inorganic Chemistry, 1992, vol. 31, No. 25, pp. 5316-5324.

Knoth, "Derivatives of Heteropolyanions. 1. Organic Derivatives of $W_{12}SiO_{40}^{4-}$, $W_{12}PO_{40}^{3-}$, and $Mo_{12}SiO_{40}^{4-}$", Journal of the American Chemical Society, Jan. 31, 1979, vol. 101, No. 3, pp. 759-760.

Mayer, "Organophosphoryl Derivatives of Trivacant Tungstophosphates of General Formula $\alpha$-A-$[PW_9O_{34}(RPO)_2]_5$: Synthesis and Structure Determination by Multinuclear Magnetic Resonance Spectroscopy ($^{31}P$, $^{183}W$)", J. Chem. Soc., Dalton Trans., 1998, pp. 7-13.

Mayer, "Organic-Inorganic Hybrids Based on Polyoxometalates. 5.[1] Synthesis and Structural Characterization of Bis(organophosphoryl)decatungstosilicates $[\gamma$-$SiW_{10}O_{36}((RPO)_2]^{4-}$", Inorganic Chemistry, 1999, vol. 38, No. 26, pp. 6152-6158.

Mayer, "Bis- and Tetrakis(organosilyl) Decatungstosilicate, $[\gamma$-$SiW_{10}O_{36}(RSi)_2O]^{4-}$ and $[\gamma$-$SiW_{10}O_{36}(RSiO)_4]^{4-}$: Synthesis and Structural Determination by Multinuclear NMR Spectroscopy and Matrix-Assisted Laser Desorption/Ionization Time-of-Flight Mass Spectrometry", Chem. Eur. J., Jan. 3, 2000, vol. 6, No. 1, pp. 105-110.

Mayer, "New Hybrid Covalent Networks Based on Polyoxometalates: Part 1. Hybrid Networks Based on Poly(ethyl methacrylate) Chains Covalently Cross-linked by Heteropolyanions: Synthesis and Swelling Properties", Chem. Mater., Feb. 2000, vol. 12, No. 2, pp. 257-260.

Mayer, "Hybrid Hydrogels Obtained by the Copolymerization of Acrylamide with Aggregates of Methacryloyl Derivatives of Polyoxotungstates. A Comparison with Polyacrylamide Hydrogels with Trapped Aggregates", Macromolecules, Jun. 13, 2000, vol. 33, No. 12, pp. 4433-4437.

Mazeaud, "Coordination Chemistry of Polyoxometalates: Rational Synthesis of the Mixed Organosilyl Derivatives of Trivacant Polyoxotungstates $\alpha$-A-$[PW_9O_{34}(tBuSiO)_3(RSi)]^{3-}$ and $\alpha$-B-$[AsW_9O_{33}(tBuSiO)_3(HSi)]^{3-}$", Angew. Chem. Int. Ed. Engl., 1996, vol. 35, No. 17, pp. 1961-1964.

Pope, Heteropoly and Isopoly Oxometalates, Springer Verlag, 1983.

Teze, "$\alpha$-, $\beta$-, and $\gamma$-Dodecatungstosilicic Acids: Isomers and Related Lacunary Compounds", Inorganic Syntheses, 1990, vol. 27, pp. 85-96.

Weeks, "Synthesis, Characterization, and Anti-Human Immunodeficiency Virus Activity of Water-Soluble Salts of Polyoxotungstate Anions with Covalently Attached Organic Groups", J. Med. Chem., Apr. 1992, vol. 35, No. 7, pp. 1216-1221.

Yang, "The Preparation and Ion-Exchange Properties of Zirconium Sulphophosphonates", Reactive Polymers, 1987, vol. 5, pp. 13-21.

International Search Report for PCT/US2009/041614, 6 pages.

Chang Gi Cho, "Synthesis and Characterization of Poly(arylene ether sulfone) Copolymers with Sulfonimide Side Groups for a Proton-Exchange Membrane", Journal of Polymer Science: Part A: Polymer Chemistry, Oct. 15, 2006, vol. 44, No. 20, pp. 6607-6014.

Rahman, "Synthesis, Characterization, and Copolymerization of a Series of Novel Acid Monomers Based on Sulfonimides for Proton Conducting Membranes", Macromolecules, Jul. 27, 2004, vol. 37, No. 15, pp. 5572-5577.

\* cited by examiner

PROTON CONDUCTING MATERIALS

CROSS-REFERENCE TO RELATED APPLICATION

This application is a divisional application of prior application Ser. No. 13/269,907, filed Oct. 10, 2011, now allowed, which is a divisional of U.S. application Ser. No. 12/429,371, filed Apr. 24, 2009, which claims the benefit of U.S. Provisional Patent Application No. 61/047,643, filed Apr. 24, 2008, the disclosure of which is incorporated by reference in its entirety herein.

GOVERNMENT RIGHTS

This disclosure was made with Government support under Cooperative Agreement DE-FG36-07GO17006 awarded by DOE. The Government has certain rights in this disclosure.

FIELD OF THE DISCLOSURE

This disclosure relates to materials that may be useful as ionomers or polymer ionomers.

BACKGROUND OF THE DISCLOSURE

In some applications, including some automotive applications, there is a desire to operate fuel cells at higher temperatures, e.g., in the neighborhood of 120° C., in part for the purpose of simplifying the cooling systems while improving the heat rejection. Higher temperatures may also provide efficiency gains in using the waste heat in combined heat and power systems. Operating at higher temperatures may also improve catalyst resistance to CO poisoning when using reformed fuels. In some applications, humidifying incoming reactant gas streams has been practiced in order to elevate the level of hydration in the proton exchange membrane (PEM), however, humidifiers add to the initial cost of a system and increase parasitic power losses during operation. Humidifying become increasingly difficult at elevated temperatures; hence there is a need for inherently higher-conducting materials to efficiently move protons with little or no water.

SUMMARY

Briefly, the present disclosure provides compounds according to the formula:

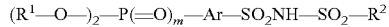

wherein each $R^1$ is independently chosen from the group consisting of hydrogen, alkyl, alkylene or aryl groups which may contain heteroatoms and which may be substituted, polymers, metals, metal oxides, metal phosphates, metal phosphonates and inorganic particles, wherein m is 0 or 1, wherein Ar is an aromatic group which may include heterocycles and polycycles and may be substituted, and wherein $R^2$ is chosen from the group consisting of alkyl, alkylene or aryl groups which may contain heteroatoms and which may be substituted, and polymers. In some embodiments, Ar is phenylene. In some embodiments, Ar is phenylene-$R^3$, wherein $R^3$ is chosen from the group consisting of hydrogen, alkyl, alkylene or aryl groups which may contain heteroatoms and which may be substituted, and polymers. In some embodiments, $R^2$ is a fluoropolymer. In some embodiments, $R^2$ is substituted with one or more acid groups selected from the group consisting of sulfonic acid groups and phosphonic acid groups.

In another aspect, the present disclosure provides compounds according to the formula:

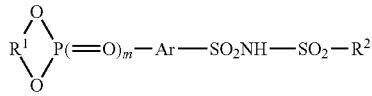

wherein $R^1$ is chosen from the group consisting of metals, metal oxides, metal phosphates, metal phosphonates and inorganic particles, wherein m is 0 or 1, wherein Ar is an aromatic group which may include heterocycles and polycycles and may be substituted, and wherein $R^2$ is chosen from the group consisting of alkyl, alkylene or aryl groups which may contain heteroatoms and which may be substituted, and polymers. In some embodiments, Ar is phenylene. In some embodiments, Ar is phenylene-$R^3$, wherein $R^3$ is chosen from the group consisting of hydrogen, alkyl, alkylene or aryl groups which may contain heteroatoms and which may be substituted, and polymers. In some embodiments, $R^2$ is a fluoropolymer. In some embodiments, $R^2$ is substituted with one or more acid groups selected from the group consisting of sulfonic acid groups and phosphonic acid groups. In some embodiments, one or more or every $R^1$ is a metal or metal oxide wherein the metal is selected from the group consisting of Zr, Ti, Th and Sn. In some embodiments, one or more or every $R^1$ is a metal or metal oxide wherein the metal is selected from the group consisting of tetravalent metals.

In another aspect, the present disclosure provides compounds according to the formula:

wherein each $R^1$ is independently chosen from the group consisting of hydrogen, alkyl, alkylene or aryl groups which may contain heteroatoms and which may be substituted, polymers, metals, metal oxides, metal phosphates, metal phosphonates and inorganic particles, wherein n is 1, 2 or 3, wherein Ar is an aromatic group which may include heterocycles and polycycles and may be substituted, and wherein $R^2$ is chosen from the group consisting of alkyl, alkylene or aryl groups which may contain heteroatoms and which may be substituted, and polymers. In some embodiments, Ar is phenylene. In some embodiments, Ar is phenylene-$R^3$, wherein $R^3$ is chosen from the group consisting of hydrogen, alkyl, alkylene or aryl groups which may contain heteroatoms and which may be substituted, and polymers. In some embodiments, $R^2$ is a fluoropolymer. In some embodiments, $R^2$ is substituted with one or more acid groups selected from the group consisting of sulfonic acid groups and phosphonic acid groups.

In another aspect, the present disclosure provides polymer electrolytes comprising a highly fluorinated backbone and first pendant groups which comprise groups according to the formula:

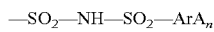

wherein Ar is an aromatic group of 5-24 carbon atoms which may include heterocycles and polycycles and may be substituted, where A is selected from the group consisting of —$SO_3H$ and —$PO_3H_2$, where n is between 1 and q, where q is one-half the number of carbons in Ar. In some embodiments the polymer electrolyte comprises a perfluorinated backbone. In some embodiments the polymer electrolyte comprises second pendant groups which comprise groups according to the formula: —$SO_3H$. In some embodiments the ratio of first to second pendant groups is p, where p is between 0.01 and 100, between 0.1 and 10, between 0.1 and 1 or between 1 and 10.

In another aspect, the present disclosure provides polymer electrolyte membranes or membrane electrode assemblies comprising the present polymer electrolytes, which may additionally comprising a porous support or may additionally be crosslinked.

In this application:

"equivalent weight" (or "EW") of a polymer means the weight of polymer which will neutralize one equivalent of base (allowing that, where sulfonyl halide substituents or other substituents that would be converted into acidic functions during use of the polymer in a fuel cell are present, "equivalent weight" refers to the equivalent weight after hydrolyzation of such groups);

"highly fluorinated" means containing fluorine in an amount of 40 wt % or more, typically 50 wt % or more and more typically 60 wt % or more; and "substituted" means, for a chemical species, substituted by conventional substituents which do not interfere with the desired product or process, e.g., substituents can be alkyl, alkoxy, aryl, phenyl, halo (F, Cl, Br, I), cyano, nitro, etc.

DETAILED DESCRIPTION

This disclosure relates to production of materials, including polymers, particles and small molecules, linked to acid-containing through the covalent bonding of materials using sulfonamide, bis sulfonyl imide and phosphonic linkages.

In another aspect, this disclosure concerns fuel cell membrane materials with an increased number of strong acid groups created in some embodiments by reaction of these acid containing molecules with acid containing organic molecules, metal oxide or phosphate particles, metal salts, heteropolyacids, and the like.

Another aspect of this disclosure involves the use of these multifunctional materials to develop crosslinked structures for improved mechanical properties or to minimize component leaching.

Materials taught in this disclosure may be used for fuel cell applications such as in the manufacture of proton exchange membranes (PEM), as catalyst additives or in tie layers designed to be thermally and chemically robust while operating within a fuel cell's harsh environment at higher temperatures and to conduct protons, with significantly higher levels of bound acidic groups, while in a low hydration state.

This disclosure describes the modification of PFSA's or other polymers by the conversion of the sulfonic acid group to a bis sulfonyl imide group with an aromatic group which can be further modified by the attachment of additional acid groups (for improved conductivity) or phosphonic acid groups or silane groups (for attachment of heteropolyacids, for the attachment of inorganic particles such as zirconia or zirconyl phosphate or for the attachment of silica particles).

This group can also be used to create cross-links. Crosslinking may be accomplished thru the use of difunctional reactants. Examples include but are not limited to: ammonia, benzene disulfonyl chloride, naphthalene disulfonyl chloride sulfonic acid sodium salt, bis-(phenyldisulfonyl anhydride) and disulfonamides (e.g. benzene disulfonamide).

Below are two schematics detailing possible linking reactions

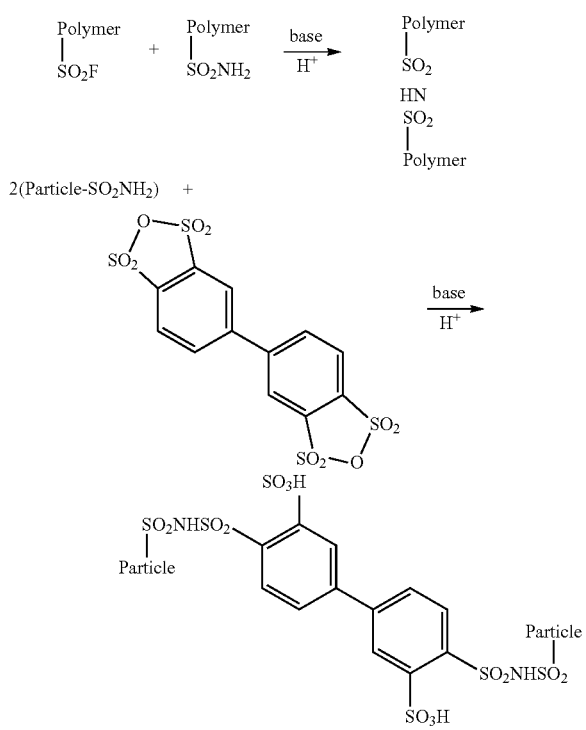

Useful reactive groups include halides, sulfonyl halides, disulfonyl anhydrides, sulfonamides, amines, phosphonic diols, acids and esters, Tungstenic diols, and the like.

Aromatic groups may be sulfonated by any suitable method. Aromatic groups may be sulfonated by use of $Na_2SO_3$, chlorosulfonic acid, trimethyl silyl sulfonic acid, sulfuric acid, or other sulfonating agents.

This disclosure further describes the attachment of small molecules containing bis sulfonyl imides to inorganic moieties such as HPA's or particles and methods of synthesizing these compounds.

This disclosure incorporates by reference the disclosures of U.S. patent application Ser. No. 12/342,370, filed Dec. 23, 2008, U.S. Pat. No. 7,285,349, issued Oct. 23, 2007, U.S. Pat. No. 7,348,088, issued Mar. 25, 2008, U.S. Pat. No. 6,727,386, issued Apr. 27, 2004, U.S. Pat. No. 6,863,838, issued Mar. 8, 2005, and U.S. Pat. No. 6,090,895, issued Jul. 18, 2000.

Polymers according to the present disclosure may be crosslinked by any suitable method, which may include methods disclosed in U.S. Pat. No. 7,179,847, issued Feb. 20, 2007; U.S. Pat. No. 7,514,481, issued Apr. 7, 2009; U.S. Pat. No. 7,265,162, issued Sep. 4, 2007; U.S. Pat. No. 7,074,841, issued Jul. 11, 2006; U.S. Pat. No. 7,435,498, issued Oct. 14, 2008; U.S. Pat. No. 7,259,208, issued Aug. 21, 2007; U.S. Pat. No. 7,411,022, issued Aug. 12, 2008; U.S. Pat. No. 7,060,756, issued Jun. 13, 2006; U.S. Pat. No. 7,112,614, issued Sep. 26, 2006; U.S. Pat. No. 7,060,738, issued Jun. 13, 2006; U.S. Pat. No. 7,173,067, issued Feb. 6, 2007; and U.S. Pat. No. 7,326,737, issued Feb. 5, 2008; the disclosures of which are incorporated herein by reference.

The scope of this disclosure should not be restricted solely to polymers electrolytes or fuel cell applications, as one could envision applications outside of fuel cell use.

Objects and advantages of this disclosure are further illustrated by the following examples, but the particular materials and amounts thereof recited in these examples, as well as other conditions and details, should not be construed to unduly limit this disclosure.

EXAMPLES

Unless otherwise noted, all reagents were obtained or are available from Aldrich Chemical Co., Milwaukee, Wis., or may be synthesized by known methods.

Example 1

Sulfonamide-Functional Polymer

A sulfonamide functional polymer was created by reacting a polymer having pendent sulfonyl fluoride groups with ammonia followed by ion exchange, as diagrammed below. As indicated, a side reaction can occur involving formation of imide crosslinks by the reaction of the sulfonamide with a second —$SO_2F$ group.

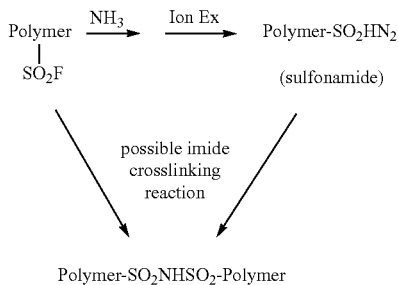

The polymer used was a copolymer of tetrafluoroethylene (TFE) and $FSO_2$—$CF_2CF_2CF_2CF_2$—O—$CF$=$CF_2$, described in U.S. patent application Ser. Nos. 10/322,254, 10/322,226 and 10/325,278, which are incorporated herein by reference. About 23 g of a 90/10 blend of a ~680 EW polymer and an 800 EW polymer was placed into a 600 ml Parr bomb with 150 g acetonitrile. The bomb was sealed up, evacuated and with low agitation chilled to −20 C. Ammonia was added to 40 psig and the temperature keep below 5 C for 6 hours. It was then allowed to warm up to room temperature overnight.

The vessel was opened and the grey solid polymer separated and dissolved in 108 g of methanol and 20 g of DI water with modest warming.

5.7 g of lithium hydroxide monohydrate and 40 g of DI water was added to the clear colorless solution and roller mixed with modest heating.

The solution was then exposed to acidified and rinsed Amberlite IR-120 ion exchange beads a total of 6 times to drop the solution pH containing polymer to ~3. An NMR spectrum of the lower pH solution shows a substantial sulfonamide peak at −115.0 with a small sulfonic acid peak at −115.7, with a peak integration ratio of 12 to 1. The solution was dried at 60 C, overnight, resulting in 12.1 g of light yellow solid. The polymer was then redissolved in acetonitrile, allowed to stand and settle. The dissolved portion was again coated out and dried, resulting in 8.7 g of slightly yellow, slightly cloudy, rigid film.

Example 2

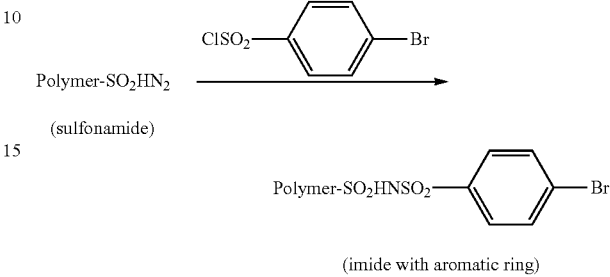

1.51 g of the sulfonamide functional perfluorinated polymer from Example 1 was dissolved in 13.7 g of dry acetonitrile. 0.85 g of 4-Bromobenzenesulfonyl chloride was added and quickly dissolved. The vial was cooled to −10 C and 1.11 g of triethylamine added and stirred. The vial was heated at 70 C for 2 hours in an oil bath. An additional 0.49 g of triethylamine was added after 2 hours. A 6% $H_2SO_4$ in water solution was used to lower the pH from ~10 to ~3. In doing so, the cloudy polymer precipitated out. This solid was redissolved quickly in acetonitrile and additional 6% $H_2SO_4$ in water solution used to drop pH to ~0.5, with triethylamine used to bring the pH back to ~2.5. Tetrahydrofuran was added in hopes of reprecipitating the polymer without success. The solution was dried down at 65 C for 3 hours, without the fine material which had settled to the bottom. 1.6 g of light tan film was recovered and an NMR spectrum showed a substantial bis sulfonylimide peak at −113.5, with no sulfonamide peak at ~−115.0 and a small sulfonic acid peak at −115.5, with a peak integration ratio of 11 to 1.

Example 3

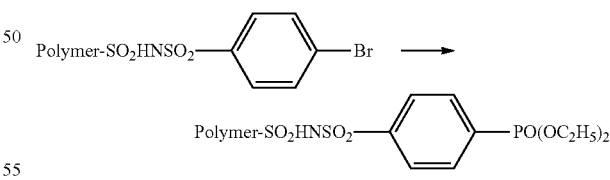

1 gm of fluoropolymer containing phenylbromide attached to the polymer via a bis sulfonylimide group, obtained in Example 2, was suspended in 30 ml EtOH. To this was added 49 mg of Palladium(II) acetate and 173 mg of triphenylphosphine followed by dropwise addition of 0.35 ml of N,N-dicyclohexylmethylamine and 0.225 ml of diethyl phosphite. The reaction mixture was heated for 30 min at 70° C. In order, to dissolve the polymer 4 ml of N-methyl pyrrolidone was added. A clear formed, was refluxed for 15 hours at 80° C. The solvent was removed in a rotary evaporator. The product obtained shows a 31P NMR signal at δ 16.2 ppm (referenced to $H_3PO_4$) confirming the formation of the phosphonate ester.

Example 4 bis phosphophenyl bis sulfonyl imide acid

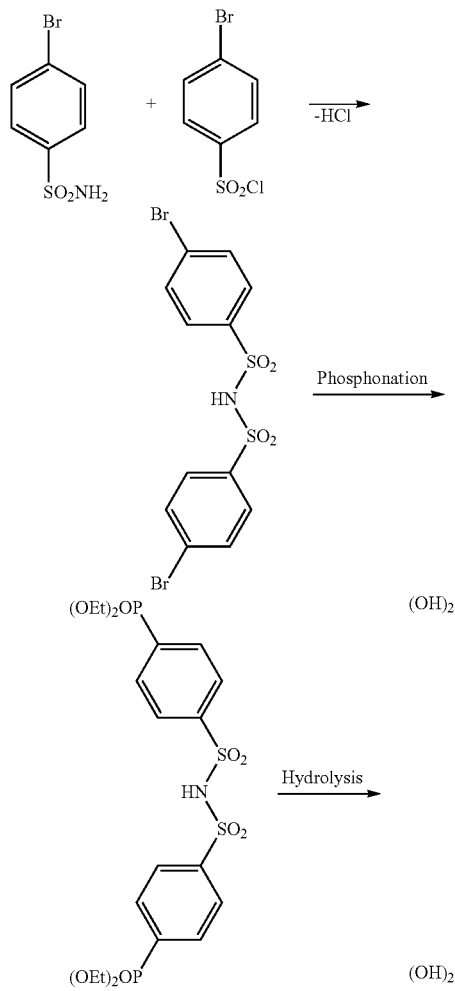

Step 1. 23.6 gm of 4-Bromobenzenesulfonamide was added to 100 ml of dry Acetonitrile in a three-necked round bottom flask. The flask was cooled to 0° C. and a water cooled reflux condenser was attached to the center neck of the flask. The flask was continuously purged with Nitrogen during the course of the reaction. 30.3 gm of Triethylamine was added to the flask under stirring. 25.6 gm of 4-Bromobenzenesulfonyl-chloride was weighed in a Nitrogen purged box and added in portions to the flask under constant stirring. 30 ml of acetonitrile was added to the mixture to wash any residual 4-bromobenzenesulfonyl chloride sticking to the neck of the round bottom flask. The mixture was stirred for ~24 hours. The triethylamine hydrochloride salt was filtered and the filtrate was concentrated to yield the brown triethylamine salt of the bis sulfonyl imide product in ~50% yield. The formation of bis sulfonyl imide product was confirmed by $^1H$ NMR and $^{13}C$ NMR.

Step 2. An oven dried flask was cooled under nitrogen and charged with 1 gm of product from step 1, palladium(II) acetate (8 mg) and triphenylphosphine (30 mg). 15 ml of Ethanol was introduced into the flask through a needle and syringe followed by dropwise addition of N,N-dicyclohexylmethylamine (1.25 ml) and diethyl phosphite (0.61 ml). The reaction mixture was refluxed for 15 hours at 80° C. The solvent was removed in a rotary evaporator to obtain the product as triethyl amine salt—a brown semisolid in 80% yield. The phosphonation was confirmed by $^{31}P$ NMR signal at δ 16.74 ppm (referenced to $H_3PO_4$).

Step 3. 1 g of step 2 product was refluxed with 20 ml of 12N HCl for 36 hours to hydrolyze the phosphonate ester. The resulting mixture was dried using a rotary evaporated to yield the hydrolyzed phosphonic acid product. The completion of the hydrolysis of the diethylphosphonate ester was confirmed by the absence of the ethyl signals at 3.99 ppm, 1.22 ppm in the final product and by the $^{31}P$ NMR: δ 12.06 ppm (referenced to $H_3PO_4$).

Example 5

(4-benzenebisulfonimide-phenyl)-phosphonic acid

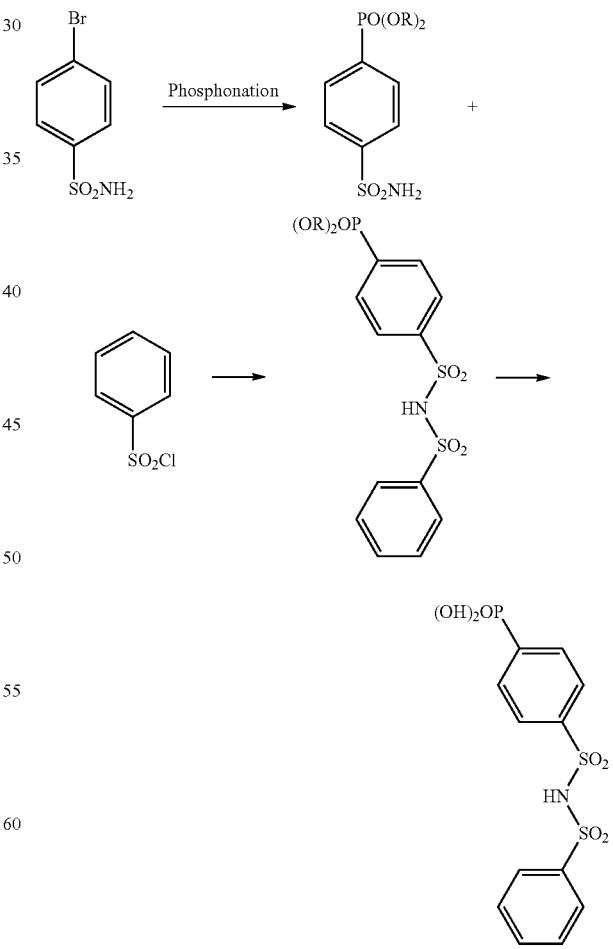

Step 1: (4-sulfamoyl-phenyl)-phosphonic acid diethyl ester

An oven dried flask was charged with 6.5 gm of 4-bromobenzenesulphonamide, 112.2 mg of palladium(II) acetate and 392.5 mg of triphenylphosphine. 100 ml of Ethanol was introduced into the flask through a needle and syringe followed by dropwise addition of 8 ml N,N-dicyclohexylmethylamine and 3.87 ml of diethyl phosphite. The reaction mixture was refluxed for 15 hours at 80° C. On cooling, slow precipitation of the product as a white solid is observed. The volume of solvent was reduced to half in a rotary evaporator and the solid precipitate was filtered through a sintered funnel under vacuum. The product was obtained as a white solid in 80% yield. $^{31}$P NMR: δ 15.83 ppm (referenced to $H_3PO_4$), $^{15}$N NMR: δ 95.5 ppm (referenced to liquid ammonia as 0 ppm through a secondary reference of glycine),

Step 2: (4-benzenedisulfonimide-phenyl)-phosphonic acid diethyl ester

An oven dried flask was charged with 2.5 g of (4-sulfamoyl-phenyl)-phosphonic acid diethyl ester (Product from step 1) and 100 ml of acetonitrile. The flask was cooled to 0° C. and to it 3.2 ml of benzene sulfonyl chloride was added dropwise followed by 8.5 ml of triethylamine. The reaction was stirred for 3 hours and triethyl amine hydrochloride salt was filtered off. Lithium salt of the product was obtained by adding 10 g of LiOH.H$_2$O to the reaction mixture. The solids were filtered and the filtrate concentrated to yield the product in 80% yield. $^{31}$P NMR: δ 16.8 ppm (referenced to $H_3PO_4$).

Step 3: (4-benzenedisulfonimide-phenyl)-phosphonic acid 18 g of product from step 2 was refluxed with 200 ml of 12N HCl for 36 hours to hydrolyze the phosphonate ester. The resulting mixture was dried using a rotary evaporated to yield the hydrolyzed phosphonic acid product in 95% yield. The completion of the hydrolysis of the diethylphosphonate ester was confirmed by the absence of the ethyl signals from the ester at 4.02 ppm and 1.23 ppm, $^{31}$P NMR: δ 11.36 ppm (referenced to $H_3PO_4$). The lithium free product was obtained by ion exchange on strongly acidic type amberlite resin column.

Example 6

0.5 gm of ZrOCl$_2$.8H$_2$O was dissolved in 30 gm of deionized water in a Polypropylene bottle. To this solution 2 gm of (50 wt %) Hydrofluoric acid was added under stirring. After 5 min 1.3 gm of phosphonic acid H$_2$O$_3$P—C$_6$H$_4$—SO$_2$NHSO$_2$—C$_6$H$_5$ synthesized in Example 5 was added to the above mixture. The polypropylene bottle containing the mixture was heated in an oil bath under stirring at 80° C. for 16 hours. The dried product was washed with methanol and centrifuged. The supernatant was decanted. The precipitate was dried in a hot air oven at 110° C. for 15 minutes. X-ray diffraction shows peaks for a layered the zirconium phosphonates solid (001 reflection at 23.5 Å, 002 reflection at 11.7 Å and 003 reflection at 7.85 Å).

Example 7

Prophetic

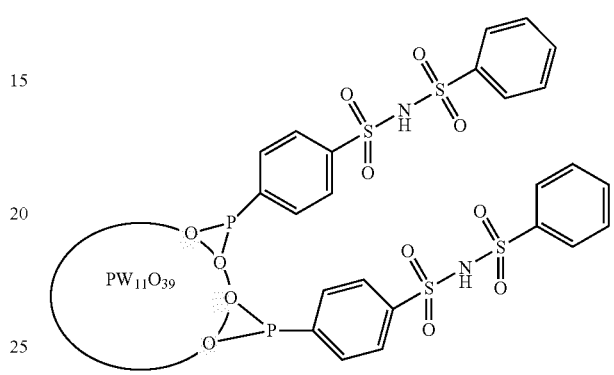

The phosphonic acid synthesized in Example 5 is attached to a lacunary heteropolyacid, such as described in U.S. patent application Ser. No. 12/266,932, filed Nov. 7, 2008, (the disclosure of which is incorporated herein by reference), by reacting the phosphonic acids with a lacunary heteropolyacid salt by the method described in Example 6.

Example 8

Perfluorinated Polymer with Side Chains According to the Formula: —O—(CF$_2$)$_4$—SO$_2$—NH—SO$_2$-PhF$_5$ 10 g of a substantially sulfonamide-functional polymer at 10% solids, made according to the process of Example 1 using 733 EW polymer, and 5.6 g of pentafluorobenzenesulfonyl chloride (from Alfa Aesar, Ward Hill, Mass., USA) were dissolved in 45 ml of Aldrich sealed acetonitrile. The addition was done under nitrogen. After allowing the mixture to stir for 1 hr, at this time all solids have dissolved in the solution, 4.25 g of Aldrich sealed triethyl amine was added to the mixture and allowed to stir for 2 hr followed by mild heating (72° C.) for an additional 15 min. Sample from the crude mixture was analyzed with NMR. The fluorine NMR shows a strong peak at −113.4 ppm which corresponds to the CF$_2$ group adjacent to the sulfur in the pentafluorosulfonylimide of the polymer.

Example 9

Perfluorinated Polymer With Side Chains According to the Formula: —O—(CF$_2$)$_4$—SO$_2$—NH—SO$_2$-PhF$_2$ The reaction described in Example 8 was carried out using 2 g of 3,5-difluorobenzenesulfonyl chloride (from Alfa Aesar, Ward Hill, Mass., USA) and 10 g of polymer at 10% solids in 45 ml of acetonitrile.

Example 10

Perfluorinated Polymer with Side Chains According to the Formula: —O—(CF$_2$)$_4$—SO$_2$—NH—SO$_2$-Ph-SO$_3$H (ortho)

1.36 g of 1, 2 benzenedisulfonyl anhydride, a synthesis of which can be found in J. Org. Chem., Vol. 48, No. 18, 1983, pg 2943-2949, was added to a reaction vessel containing 48 g of a substantially sulfonamide-functional polymer at 8.8% solids dissolved in dry acetonitrile, made according to the process of Example 1 using 812 EW polymer. 2.1 g of triethylamine was then added the solution, mixed well and allowed to react overnight at room temperature. Solution NMR shows a significant peak at −113.1 ppm which corresponds to the CF$_2$ group adjacent to the sulfur in the pentafluorosulfonylimide of the polymer. 1.1 g of 2M LiOH was then added, mixed well and the upper solution dried down at 65 C to produce a clear, slight tan film of a PFSA with side chains containing primarily a bissulfonylimide benzene-2 sulfonic group. Building a lower EW ionomer from a higher EW precursor polymer may result in higher backbone crystallinity at a given EW.

Example 11

Perfluorinated Polymer with Side Chains According to the Formula: —O—(CF$_2$)$_4$—SO$_2$—NH—SO$_2$-Ph-SO$_3$H (meta)

1.46 g of 1, 3 benzenedisulphonyl chloride (obtained from Lancaster in Morecambe, England) was added with 5 g of acetonitrile to 1.57 g of a substantially sulfonamide-functional polymer at 10% solids dissolved in acetonitrile, made according to the process of Example 1 using 812 EW polymer. 0.092 g of deionized water was then added and the container emptied into a 3 neck flask, maintaining a nitrogen atmosphere. The container was rinsed with 3.5 g of acetonitrile and also added to the flask. Add 3 mls of triethyl amine to 17 ml of acetonitrile in an addition funnel and slowly drip into the flask, over 3 hours, at room temperature. NMR of the solution shows a significant peak at −113.1 ppm. Add 2M LiOH solution to create a very basic solution, a brown precipitate forms. Retain solid and rinse 3 times with acetonitrile. Rinse solids with 2M LiOH solution and then 5 times with deionized water. Rinse solid with 10% H2SO4/deionized water mixture to lower pH, followed by 5 DI water rinses. Add 15.8 g of methanol and dissolve solid with modest heating. Rinse flask with 90/10 methanol/water mixture and run everything through an ion exchange column of amberlite IR-120 beads twice, diluting with 90/10 methanol/water mixture to help the flow. Dry down the polymer solution using nitrogen flow to create a film. The resulting polymer had, by calculation, an EW of about 550, yet it was prepared from a precursor polymer with an EW of 812. Building a lower EW ionomer from a higher EW precursor polymer may result in higher backbone crystallinity at a given EW.

Example 12-15

Prophetic

The polymers obtained in Examples 8 and 9 are sulfonated by reaction with Na$_2$SO$_3$ to obtain acidic polymers with pendent disulfonated aromatic groups bound via sulfonyl imide functions. The polymers obtained in Examples 10 and 11 are sulfonated by to obtain acidic polymers with pendent disulfonated aromatic groups bound via sulfonyl imide functions. The polymers so obtained are further sulfonated to obtain acidic polymers with pendent polysulfonated aromatic groups bound via sulfonyl imide functions.

Example 16

Proton Conductivity

Proton conductivity was measured using a standard, in-plane, 4 point probe conductivity apparatus with platinum electrodes, commercially available form Bekktech Inc., Loveland Colo. The cell was electrically connected to a potentiostat (Model 273, Princeton Applied Research) and an Impedance/Gain Phase Analyzer (SI 1260, Schlumberger). AC impedance measurements was performed using Zplot and Zview software (Scribner Associates). Temperature and relative humidity were controlled with a constant humidity oven (TestEquity Model 1000H).

Conductivity was measured for the polymer of Example 10, the polymer of Example 11 and a polymer of about 800 EW essentially similar to the precursor polymer used to make the polymers of Examples 10 and 11. Thus all three polymers would be expected to have similar backbone crystallinity, had the polymer backbone of a polymer with an EW of about 800, however, the polymers of Examples 10 and 11 expected to have an EW of about 550 (by calculation). Conductivity was also measured for a similar polymer of about 650 EW. The polymers of Examples 10 and 11 showed improved conductivity at relative humidities of 50% or above. At relative humidities of 65% or higher, the polymers of Examples 10 and 11 demonstrated conductivity comparable to the 650 EW polymer. At a relative humidity of 35%, the polymers of Examples 10 and 11 demonstrated conductivity comparable to the 800 EW polymer. At a relative humidity of 50%, the polymers of Examples 10 and 11 demonstrated conductivity intermediate between the 650 EW and 800 EW polymers.

What is claimed is:

1. A compound according to the formula:

$R^1{}_n$—Ar—SO$_2$NH—SO$_2$—R$^2$ wherein each R$^1$ is independently chosen from the group consisting of metal oxides, metal phosphates, metal phosphonates and inorganic particles, wherein n is 1, 2 or 3, wherein Ar is an aromatic group which may include heterocycles and polycycles and may be substituted, and wherein R$^2$ is a polymer.

2. The compound according to claim 1, wherein n is 1.
3. The compound according to claim 1, wherein n is 2.
4. The compound according to claim 1, wherein Ar is a phenyl.
5. The compound according to claim 1, wherein Ar is fluorinated.
6. The compound according to claim 1, wherein Ar is perfluorinated.
7. The compound to claim 1, comprising a perfluorinated backbone.
8. The compound according to claim 1, wherein Ar is a first pendant group, and wherein the compound further comprises a second pendant group which comprises a group according to the formula: —SO$_3$H.
9. The compound according to claim 8, wherein the ratio of first to second pendant groups is p, where p is between 0.01 and 100.

10. The compound according to claim 8, wherein the ratio of first to second pendant groups is p, where p is between 0.1 and 10.

11. The compound according to claim 8, wherein the ratio of first to second pendant groups is p, where p is between 0.1 and 1.

12. The compound according to claim 8, wherein the ratio of first to second pendant groups is p, where p is between 1 and 10.

13. A compound according to claim 1, wherein $R^1$ is chosen from the group consisting of metal phosphates and metal phosphonates.

14. A polymer electrolyte membrane comprising the compound according to claim 1.

15. The polymer electrolyte membrane according to claim 14 additionally comprising a porous support.

16. A polymer electrolyte membrane comprising the compound according to claim 14 after crosslinking.

17. A fuel cell membrane electrode assembly comprising an electrode comprising the compound according to claim 1.

* * * * *

UNITED STATES PATENT AND TRADEMARK OFFICE
CERTIFICATE OF CORRECTION

PATENT NO. : 8,481,227 B2
APPLICATION NO. : 13/529706
DATED : July 9, 2013
INVENTOR(S) : Steven J. Hamrock et al.

It is certified that error appears in the above-identified patent and that said Letters Patent is hereby corrected as shown below:

Title Page, Column 1 (Other Publications)
Line 17, delete "Benzenedisulfinic" and insert -- Benzenedisulfonic --, therefor.

Title Page 2, Column 1 (Other Publications)
Line 9, delete "[PW$_9$O$_{34}$(RPO)$_2$]$_5$.:" and insert -- [PW$_9$O$_{34}$(RPO)$_2$]$^{5-}$: --, therefor.

In the Specification

Column 5
Line 49, delete "5 C" and insert -- 5° C. --, therefor.

Line 66, delete "60 C," and insert -- 60° C., --, therefor.

Column 6
Line 26, delete "-10 C" and insert -- -10° C. --, therefor.

Lines 27-28, delete "70 C" and insert -- 70° C. --, therefor.

Line 37, delete "65 C" and insert -- 65° C. --, therefor.

Column 9
Line 20, delete "glycine)," and insert -- glycine). --, therefor.

Column 10
Line 29, delete "heterpolyacid," and insert -- heteropolyacid, --, therefor.

Column 11
Line 18, delete "65 C" and insert -- 65° C. --, therefor.

Signed and Sealed this
Twenty-ninth Day of October, 2013

Teresa Stanek Rea
*Deputy Director of the United States Patent and Trademark Office*

Column 12

Line 12, delete "form" and insert -- from --, therefor.